United States Patent
Pandey et al.

(10) Patent No.: US 9,150,892 B2
(45) Date of Patent: Oct. 6, 2015

(54) **PROCESS OF PRODUCING ARGININE EMPLOYING *CORYNEBACTERIUM GLUTAMICUM* ATCC 21831 OR *CORYNEBACTERIUM GLUTAMICUM* ATCC 21493 IN AN AFERMANTATION MEDIUM COMPRISING CASSAVA BAGASSE OR JACKFRUIT SEED AS A CARBON SOURCE**

(75) Inventors: Ashok Pandey, Trivandrum (IN); K. Madhavan Nampoothiri, Trivandrum (IN); Ravi Subramanyam, Mumbai (IN)

(73) Assignees: Colgate-Palmolive Company, New York, NY (US); Council of Scientific and Industrial Research (IN)

( * ) Notice: Subject to any disclaimer, the term of this patent is extended or adjusted under 35 U.S.C. 154(b) by 159 days.

(21) Appl. No.: 13/577,629

(22) PCT Filed: Feb. 25, 2010

(86) PCT No.: PCT/US2010/025371
§ 371 (c)(1),
(2), (4) Date: Aug. 23, 2012

(87) PCT Pub. No.: WO2011/106002
PCT Pub. Date: Sep. 1, 2011

(65) Prior Publication Data
US 2012/0309061 A1  Dec. 6, 2012

(51) Int. Cl.
*C12P 1/00* (2006.01)
*C12N 1/20* (2006.01)
*C12P 13/10* (2006.01)

(52) U.S. Cl.
CPC ..................................... *C12P 13/10* (2013.01)

(58) Field of Classification Search
CPC combination set(s) only.
See application file for complete search history.

(56) References Cited

U.S. PATENT DOCUMENTS

| | | | |
|---|---|---|---|
| 3,222,258 A | 12/1965 | Iizuka et al. | |
| 3,440,141 A | 4/1969 | Douros, Jr. et al. | |
| 3,723,249 A | 3/1973 | Kubota et al. | |
| 3,734,829 A | 5/1973 | Chibata et al. | |
| 3,849,250 A | 11/1974 | Nakayama et al. | |
| 3,878,044 A | 4/1975 | Kubota et al. | |
| 4,086,137 A | 4/1978 | Nakayama et al. | |
| 4,430,430 A | 2/1984 | Momose et al. | |
| 5,196,326 A | 3/1993 | Kuronuma et al. | |
| 6,897,048 B2 | 5/2005 | Sakanyan et al. | |
| 7,267,967 B1 | 9/2007 | Eikmanns et al. | |
| 2009/0196954 A1 | 8/2009 | Alt et al. | |

FOREIGN PATENT DOCUMENTS

| CN | 101591678 | 12/2009 |
|---|---|---|
| GB | 1278917 | 6/1972 |
| GB | 1351518 | 5/1974 |
| JP | H05-003793 A | 1/1993 |
| JP | H06-311891 | 11/1994 |
| WO | WO 2009/093703 | 7/2009 |

OTHER PUBLICATIONS

Prakash et al. "Artocarpus heterophyllus (jackfruit): an overview", Pharmacognosy Reviews, 2009, 3:353-358.
Achi, O. K. et al., "Production of a raw starch saccharifying amylase by *Bacillus alvei* grown on different agricultural substrates," World J. Microbiol. and Biotech., vol. 8, 1992, pp. 206-207.
Ahmed, S. U. et al., "Enrichment of γ-linolenic acid in the lipid extracted from *Mucor zychae* MTCC 5420," Food Research International, vol. 42, 2009, pp. 449-453.
Ajayi, I. A., "Comparative study of the chemical composition and mineral element content of *Artocarpus heterophyllus* and *Treculia africana* seeds and seed oils," Bioresource Technology, vol. 99, 2008, pp. 5125-5129.
Babitha, S. et al., "Jackfruit Seed—A Novel Substrate for the Production of *Monascus* Pigments through Solid-State Fermentation," Food Technol. Biotechnol., vol. 44, No. 4, 2006, pp. 465-471.
Elkholy, H. et al., "The World Cassava Production: An Overview," J. Root Crops, vol. 26, No. 2, 2000, pp. 1-5.
Garcia-Reyes, R. B. et al., "Contribution of agro-waste material main components (hemicelluloses, cellulose, and lignin) to the removal of chromium (III) from aqueous solution," J. Chem. Technol. Biotechnol., vol. 84, 2009, pp. 1533-1538.
Hermann, T., "Industrial production of amino acids by coryneform bacteria," J. of Biotechnology, vol. 104, 2003, pp. 155-172.
Jianhua, G. et al., "Kinetic Study and Modelling on L-Arginine Fermentation," Chinese Journal of Biotechnology, vol. 9, No. 1, 1993, pp. 9-18.
John, R. P. et al., "Simultaneous Saccharification and Fermentation of Cassava Bagasse for L-(+)-Lactic Acid Production Using *Lactobacilli*," Applied Biochemistry and Biotech., vol. 134, 2006, pp. 263-272.
John, R. P. et al., "Solid-state fermentation for L-lactic acid production from agro wastes using *Lactobacillus delbrueckii*," Process Biochemistry, vol. 41, 2006, pp. 759-763.
Kisumi, M. et al., "Production of L-Arginine by Arginine Hydroxamate-Resistant Mutants of *Bacillus subtilis*," Applied Microbiology, vol. 22, No. 6, Dec. 1971, pp. 987-991.
Kumar, S. et al., "Proximate Composition of Jack Fruit Seeds," J. Fd. Sci. Technol., vol. 25, No. 5, 1988, pp. 308-309.
Pandey, A. et al., "Biotechnological potential of agro-industrial residues. II: cassava bagasse," Bioresource Technology, vol. 74, No. 1, Aug. 2000, pp. 81-87.
Prado, F. C. et al., "Relation between Citric Acid Production by Solid-State Fermentation from Cassava Bagasse and Respiration of *Aspergillus niger* LPB 21 in Semi-Pilot Scale," Brazilian Archives of Biology and Technology, vol. 48, Special n.:, Jun. 2005, pp. 29-36.

(Continued)

*Primary Examiner* — Kagnew H Gebreyesus

(57) ABSTRACT

Disclosed are processes for producing Arginine by fermentation in which sugars obtained by enzymatic starch hydrolysis from inexpensive starch containing agro-wastes, such as Cassava bagasse and Jackfruit seed powder, are fermented in the presence of microorganisms to produce a fermentated liquor containing Arginine, and recovering Arginine from the liquor. The process can economically be scaled up for the production of Arginine from unrefined sugar sources as it produced Arginine in higher yields, when compared to more expensive synthetic carbon sources, like dextrose or sucrose.

17 Claims, No Drawings

(56) References Cited

OTHER PUBLICATIONS

Ramadas, N. V. et al., "Polyhydroxybutyrate production using Agro-industrial Residue as Substrate by *Bacillus sphaericus* NCIM 5149," Brazilian Archives of Biology and Technology, vol. 52, No. 1, Jan. 2009, pp. 17-23.

Ramadas, N. V. et al., "A statistical approach for optimization of polyhydroxybutyrate production by *Bacillus sphaericus* NCIM 5149 under submerged fermentation using central composite design," Applied Biochemistry and Biotechnology, vol. 162, No. 4, Oct. 2010, pp. 996-1007.

Sasaki, H. et al., "Screening of Microorganisms for Raw Starch Saccharifying Enzyme Production," Agric. Biol. Chem., vol. 50, No. 6, 1986, pp. 1661-1664.

Tomasini, A. et al., "Gibberellic acid production using different solid-state fermentation systems," World J. of Microbiology & Biotechnology, vol. 13, 1997, pp. 203-206.

Utagawa, T., "Production of Arginine by Fermentation," Journal of Nutrition, vol. 134, 2004, pp. 2854S-2857S.

Yoshida, H. et al., "L-Arginine Production by Arginine Analog-resistant Mutants of Microorganisms," Agric. Biol. Chem., vol. 45, No. 4, 1981, pp. 959-963.

International Search Report & Written Opinion of the International Searching Authority for corresponding International Application No. PCT/US2010/025371, mailed Mar. 8, 2011.

Babitha et al., 2007, "Solid-state fermentation for the production of Monascus pigments from jackfruit seed," Bioresource Technology 98:1554-1560.

Kislukhina, O.V., "Enzymes in the Production of Foods and Animal Feeds," Moscow: DeLi Print, 2002, p. 159.

Kawaguti et al., 2007, "Isomaltulose production using free cells: optimisation of a culture medium containing agricultural wastes and conversion in repeated-batch processes," J. Ind. Microbiol. Biotechnol. 34:261-269.

The GEF Small Grants Programme, 2012, "Pellettizing Organic Fertilizer," Community Action Global Impact, http://sgp.undp.org/web/projects/7960/pellettizing_organic_fertilizer.html.

Woiciechowski et al., 2002, "Acid and Enzymatic Hydrolysis to Recover Reducing Sugars from Cassava Bagasse: an Economic Study," Brazilian Arch. Biology Technol. 45(3):393-400.

PROCESS OF PRODUCING ARGININE EMPLOYING CORYNEBACTERIUM GLUTAMICUM ATCC 21831 OR CORYNEBACTERIUM GLUTAMICUM ATCC 21493 IN AN AFERMANTATION MEDIUM COMPRISING CASSAVA BAGASSE OR JACKFRUIT SEED AS A CARBON SOURCE

CROSS-REFERENCE TO RELATED APPLICATIONS

The present application is a national stage entry under 35 U.S.C. 371 of International Patent Application No. PCT/US2010/025371, filed Feb. 25, 2010, the entirety of which is hereby incorporated by reference.

BACKGROUND OF THE INVENTION

The present invention relates to a bioprocess for producing L-arginine by fermentation. The embodiments include reducing sugars obtained by enzymatic starch hydrolysis from inexpensive starch containing agro-wastes, such as Cassava bagasse and Jackfruit seed powder, both of which are abundant in Asian and African countries. The process can economically be scaled up for the production of arginine from unrefined sugar sources by replacing expensive synthetic carbon sources like dextrose or sucrose.

The growing market demand for amino acids made academia and industrialists develop new methods to produce amino acids efficiently and cost effectively. This technological race facilitated the manufacture of amino acids mainly by four methods—extraction from protein hydrolysates, chemical synthesis, enzymatic hydrolysis and fermentation. From the economic standpoint, fermentation is found to be industrially feasible and is widely used except in a few cases where high production yield has not been achieved. The economy of this method mainly depends on the cost of the carbon source, fermentation yield, purification yield and productivity in the overall process. Growth in market value for amino acids produced by coryneform bacteria led to significant developments in bioprocess and downstream processing technology. This led to the efforts to increase productivity and decrease production costs. (Thomas Hermann, "Industrial production of amino acids by coryneform bacteria," *Journal of Biotechnology* 104 155-172 (2003)). Hence, any natural process that has an impact on the yield of L-arginine is in demand for utilization in industrial practice.

L-Arginine is a conditionally essential amino acid, so called, depending on the developmental stage and health status of the individual. Arginine stimulates the immune system by increasing the output of T-cells, helps in vasodilatation, in maintaining muscular health, removing ammonia from body and the release of hormones. L-Arginine has been manufactured conventionally by three methods: (i) extractions from protein hydrolysates; (ii) chemical synthesis; and (iii) enzymatic hydrolysis (Takishi Utagawa, "Production of Arginine by fermentation," *J. Nutr.* 134:2854S-2857S (2004)). Later it was discovered that L-Arginine can be produced in small amounts by hydrocarbon assimilating wild strains of *Corynebacterium* and *Brevibacterium* (U.S. Pat. Nos. 3,222,258 and 3,440,141) and its mutant strains produced even higher amounts from carbohydrates (British Patent No. 1,278,917).

Among regulatory mutants of various micro organisms, *Corynebacterium glutamicum* showed higher production of L-arginine (Hajime Yoshida, Kazumi Araki and Kiyoshi Nakayama, "Arginine Production by Arginine Analog-resistant Mutants of Microorganisms," *Agric. Biol. Chem.*, 45 (4), 959-963 (1981). Some of the most typical arginine producing mutants are of the genus *Corynebacterium* resistant to 2-thiazolealanine (U.S. Pat. Nos. 3,723,249 and 3,878,044) and canavanine (U.S. Pat. No. 3,849,250; UK Patent No. 1,351, 518). Mutants of the genus *Bacillus* (U.S. Pat. Nos. 3,734,829 and 4,086,137, 4,430,430) and *Escherichia* (U.S. Pat. Nos. 4,430,430, 6,897,048) also are also found to produce Arginine in substantial amounts.

The production of L-Arginine in a fair amount by microbial fermentation was first reported by Kisumi et al, "Production of L-Arginine by Arginine Hydroxamate-Resistant Mutants of *Bacillus subtilis*," *Appl. Microbiol.* 22, 987 (1971). Oxygen supply is known to have an important influence on aerobic amino acids production by microorganisms (Takishi Utagawa, "Production of Arginine by fermentation," *J. Nutr.* 134: 2854S-2857S (2004)). Growth under anaerobic condition often leads to formation of toxic by-products such as acetic acid and ethanol, which in turn strongly inhibit L-arginine production (J. Gong, J. Ding, H. Huang, Q. Chen, Kinetic study and modeling on L-arginine fermentation. *Chin. J. Biotech.* 9 (1) 9-18 (1993).)

Cassava (*Manihot esculents*) bagasse has been used for the production of L-(+)-lactic acid by *Lactobacillus casei* and *Lactobacillus delbrueckii*. (Rojan P. John, K. Madhavan Nampoothiri and Ashok Pandey, *Applied Biochemistry and Biotechnology*, Vol 34, p 263-272 (2006); Rojan P. John, K. Madhavan Nampoothiri and Ashok Pandey, "Solid state fermentation for L-lactic acid production from agro wastes using *Lactobacillus delbrueckii*," *Process Biochemistry*, Vol. 41 p:759-763 (2006). It was also used in production of gibberellic acid (A. Tomasini l, C. Fajardo and J. Barrios-Gonza'lez, "Gibberellic acid production using different solid-state fermentation systems," Vol 13. p 203-206 (1997)) and citric acid by SSF (Flavera Camargo Prado, Luciana Porto de Souza Vandenberghe and Carlos Ricardo Soccol, "Relation between Citric Acid Production by Solid-State Fermentation from Cassava Bagasse and Respiration of *Aspergillus niger* LPB Semi-Pilot Scale," *Brazilian archives of Biology and Technology*, Vol. 48, Special n.: pp. 29-36 (2005)). Recently, Ubaid et al reported the use for gamma linolenic acid production (Syed Ubaid et al., "Enrichment of γ-linolenic acid in the lipd extracted from *Mucor zychae* MTCC5420," *Food Research International*, Volume 42, issue 4, May 2009, Pages 449-453).

Similarly, Jack fruit seed powder has been used in the production of pigments (Sumathy Babitha, Carlos R. Soccol and Ashok Pandey, "Jackfruit Seed—A Novel Substrate for the Production of Monascus Pigments through Solid-State Fermentation," *Food Technol. Biotechnol,* 44 (4) 465-471 (2006)) and in production of Poly hydroxybutyrate (Ramadas NV, Soccol CR, Pandey A Appl Biochem Biotechnol, "A Statistical Approach for Optimization of Polyhydroxybutyrate Production by *Bacillus sphaericus* NCIM 5149 under Submerged Fermentation Using Central Composite Design" *Appl. Biochem. Biotechnol.* (2009)).

Some of the disadvantages of the existing fermentation process of Arginine include, for example, the lack of wild type cultures capable of arginine production unlike in the case of glutamate, where wild *C. glutamicum* is capable of producing large amounts. It also has been difficult to produce auxotrophic mutants capable of arginine production, and there is a need for genetic engineering for strain improvement suited to arginine production. In addition, the production costs of producing arginine are relatively high due to the use of pure glucose as the sole carbon source. Hence, inexpensive alternatives to enhance the yield using the available strains are in desirable.

SUMMARY OF THE INVENTION

The following specification particularly describes and ascertains the nature of this invention and the manner in which it is to be performed. "Microbial production of L-arginine using a production medium containing the hydrolysates of agro residual substrates, which are starchy in nature like jack fruit seed powder or cassava bagasse, as the main carbon source which were not been tried before for the production of amino acids like arginine using *Corynebacterium glutamicum*"

It is a feature of an embodiment of the present invention to make use of hydrolysates made from locally available agro waste materials to replace pure sugars to grow *Corynebacterium gluctamicum* strains capable of amino acid production. It is an additional feature of an embodiment of the present invention to develop a bio process suitable for producing L-Arginine using the hydrolysates of agro-waste materials as the main carbon source and fermenting the carbon source in the presence of *Corynebacterium glutamicum*. It is an additional feature of an embodiment of the invention to purify arginine from the fermentation liquor after fermentation.

In accordance with a feature of an embodiment, there is provided a method of making arginine by fermentation of agro-wastes comprising subjecting agro-waste to fermentation in the presence of at least one of *Corynebacterium glutamicum* ATCC 21831 or *Corynebacterium glutamicum* ATCC 21493 to produce a fermented liquor containing arginine, and recovering the arginine from the fermented liquor.

In accordance with another feature of an embodiment, there is provided a method of making L-arginine from starch-containing agro-waste materials selected from cassava bagasse, jack fruit seed powder, and mixtures thereof, comprising enzymatically hydrolyzing the agro-waste materials preferably such that from 55 to 85%, preferably from 60% to 75%, and even more preferably from 65-68% of the agro-waste substrate is converted to reducing sugars; fermenting the reducing sugars (preferably as the sole carbon source) in the presence of at least one of *Corynebacterium glutamicum* ATCC 21831 or *Corynebacterium glutamicum* ATCC 21493 to produce a fermented liquor containing arginine, and recovering the arginine from the fermented liquor.

These and other features and advantages of the present invention will be readily apparent from the Detailed Description that follows.

DETAILED DESCRIPTION

The following definitions and non-limiting guidelines must be considered in reviewing the description of this invention set forth herein. The headings (such as "Background" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art.

The expression "agro-waste" denotes any waste resulting from the processing of agricultural products. Various forms of agro-waste are described in, for example, PRODUCTS FROM WASTE (INDUSTRIAL AND AGRO WASTE), National Institute of Industrial Research, (2003); Garcia-Reyes Refugio, et al., "Contribution of agro-waste material main components (hemicellusoses, cellulose, and lignin) to the removal of chromium (III) from aqueous solution," J. of Chem. Tech. & Biotech., Vol. 84, No. 10, 1522-1538 (Oct. 10, 2009). In preferred embodiments, agro-wastes include bagasse, cellulose, lignin, hemicellulose, seed powder, Cassava bagasse, or jack fruit seed powder.

The present invention includes a method of making arginine by fermentation of agro-wastes comprising subjecting agro-waste to fermentation in the presence of at least one of *Corynebacterium glutamicum* ATCC 21831 or *Corynebacterium glutamicum* ATCC 21493, preferably at a temperature within the range of from 20° C. to 50° C. and a pH within the range of 5 to 8, for a period of from 12 hours to 2 weeks, to produce a fermented liquor containing arginine, and recovering the arginine from the fermented liquor.

The use of agro-waste materials as the main carbon source for various microbial metabolite productions such as enzymes, organic acids like lactic acid, pigments were reported. While not intending on being bound by any theory, the present inventors believe that the biotechnological processes for the production of amino acids from such cheap raw materials can be improved further to make them competitive with chemically derived processes. For example, two substrates were selected by the inventors, taking into account their high starch content and successful prior use in various bioprocesses—Jackfruit and Cassava bagasse.

Jackfruit (*Artocarpus heterophyllus*) is one of the most popular tropical fruits grown in Asia. Largest of all the tree borne fruits, jackfruit contains 100 to 300 seeds in a single fruit. Seeds make up around 10-15% of the total fruit mass and have high carbohydrate and protein contents (S. Kumar, A.B. Singh, A.B. Abidi, R.G. Upadhyay, A. Singh, "Proximate composition of jackfruit seeds,"J. Food Sci. Technol. 25 141-152 (1988)).

Seeds normally are discarded or steamed and eaten as a snack or used in some local dishes. The seeds are dried and powdered to get the jackfruit seed powder or flour. Sugars obtained from the flour after starch hydrolysis can be effectively used in fermentative production of organic compounds. The jackfruit seed starch had a narrower gelatinization temperature range and required less gelatinization energy compared with modified starches which in turn reduce the cost of starch hydrolysis. The physico-chemical properties of Jack fruit seeds are described in Table 1 below.

TABLE 1

Physico chemical composition of jack fruit seed

| Parameter | Species *Artocarpus heterophyllus* Lam. |
|---|---|
| Moisture | 2.78 |
| Ash | 6.72 |
| Crude Protein | 20.19 |
| Crude Fat | 11.39 |
| Crude Fiber | 7.10 |
| Carbohydrate | 51.82 |

Source: Ibironke Adetolu Ajayi, "Comparative study of the chemical composition and mineral element content of *Artocarpus heterophyllus* and *Treculia africana* seeds and seed oils." *Bioresource Technology*, Vol 99 (11), 5125-5129 (2007).

Cassava (*Manihot esculenta* Cranz), tropical root crop, is the third most important source of calories in the tropics, rice and corn. Cassava ranks the fourth among the staple food crops in the world and consumed more than 800 million people [Elkholy H, Eltantawy A, "The world of cassava production; an overview," *Journal of Root Crops*, 26; 1-5 (2000)). Industrial processing of cassava tubers is mainly done to isolate flour and starch, which generates more liquid and sold residues (processing for flour generates solid residues while for starch generates more liquid residues). Solid residues include brown peel, inner peel unusable roots, bagasse and flour refuse, among which bagasse is the main residue. Processing about 250-300 t of fresh tubers results about 280 t of wet cassava bagasse. Cassava bagasse is made up fibrous root material and contains starch that physically process could not be executed. Poor processing conditions may result even higher concentrations of starch in cassava bagasse. The physico-chemical composition of cassava bagasse is shown in Table 2 below.

TABLE 2

Physico-chemical composition of Cassava bagasse

| Composition | Soccol (1994) | Cereda (1994) | Sterz (1997) | Vandenberghe (1998) |
|---|---|---|---|---|
| Moisture | 5.02 | 9.52 | 10.70 | 11.20 |
| Protein | 1.57 | 0.32 | 1.60 | 1.61 |
| Lipids | 1.06 | 0.83 | 0.53 | 0.54 |
| Fibers | 50.55 | 14.88 | 22.20 | 21.10 |
| Ash | 1.10 | 0.66 | 1.50 | 1.44 |
| Carbohydrate | 40.50 | 63.85 | 63.40 | 63.00 |

Source: Pandey A., Soccol C. R., Nigam P., Soccol V T, Vandenberghe LPS, Mohan R, "Biotechnology potential of agro-industrial residues, II: cassava bagasse, *Bioresource Technology* 74: 81-87 (2000).

The Arginine, preferably L-Arginine, can be produced by fermenting agro-wastes such as those described above, alone or in combination, in the presence of microorganisms to produce a mixture containing Arginine, and then optionally separating the Arginine from the mixture. Suitable microorganisms include those selected from the group consisting of *Brevibacterium lactofermentum* ATCC 21798, *Brevibacterium lactofermentum* ATCC 21799, *Brevibacterium lactofermentum* ATCC 21800, *Brevibacterium lactofermentum* ATCC 21801, *Brevibacterium lactofermentum* ATCC 21086, *Brevibacterium flavum* ATCC 21475, *Brevibacterium flavum* ATCC 21127, *Brevibacterium flavum* ATCC 21128, *Brevibacterium flavum* ATCC 21129, *Brevibacterium flavum* ATCC 21474, *Brevibacterium flavum* ATCC 21493, *Brevibacterium flavum* ATCC 21406, *Brevibacterium flavum* ATCC 21605, *Brevibacterium ammoniagenes* ATCC 19355, *Corynebacterium acetoacidophilum* ATCC 21476, *Corynebacterium acetoacidophilum* ATCC 21407, *Corynebacterium glutamicum* ATCC 21831, *Corynebacterium glutamicum* ATCC 13286, *Corynebacterium glutamicum* ATCC 21659, *Corynebacterium glutamicum* ATCC 21339, *Corynebacterium acetoglutamicum* ATCC 21491, and mixtures thereof.

The preferred microorganisms for use in the present invention are the mutant strains of *Corynebacterium glutamicum*, particularly arginine analog resistant mutants, designated as *Corynebacterium glutamicum* ATCC 21831 (U.S. Pat. No. 3,849,250, the disclosure of which is incorporated by reference herein in its entirety) and *Corynebacterium glutamicum* ATCC 21493 (*Brevibacterium flavum* ATCC 21493) (U.S. Pat. No. 5,196,326, the disclosure of which is incorporated by reference herein in its entirety) from American Type Culture Collection. The cultures preferably are maintained in LBG medium (Luria Bertani broth supplemented with glucose) and are subcultured every two weeks.

It is preferred in the present invention that the culture medium employed is a natural medium comprised of preferred amounts of carbon sources, nitrogen sources, inorganic salts and small amounts of minor inorganic nutrients required for the growth of the strains used. Preferred carbon sources in the present invention include glucose or starch hydrolysates of any starch-containing material, preferably cassava bagasse or Jack fruit seed powder obtained by their enzymatic hydrolysis using suitable starch saccharifying enzymes. Starch saccharifying enzymes are known in the art. Suitable starch saccharifying enzymes include those described in, for example, Sasaki, et al., "Screening of Microorganisms for Raw Starch Saccharifying Enzyme Production," *Agric. Biol. Chem.*, 50(6), 1661-1664 (1986), Achi, et al., "Production of a raw starch saccharifying amylsase by *Bacillus alvei* grown on different agricultural substrates," *World J. Microbiol. And Biotech.*, 8, 206-207 (1991). These include, for example, amylases, glucoamylases, pullulanases, *Corticium rolfsii*

AHU 9627, and the like. The hydrolysis process can be optimized for each substrate using techniques known in the art, along with the guidelines provided herein. In a preferred embodiment, the fermentation of starch hydrolysates of Cassava baggase and/or Jack fruit seed powder provides a greater yield than the fermentation of pure sugars such as dextrose, using the same fermentation microorganisms.

As nitrogen sources, inorganic nitrogen salts like ammonium chloride and other conventional organic nitrogen sources like Nz amine, Caseine hydrolysate, corn steep liquor etc can be used. Inorganic salts of potassium monohydrogen phosphate, potassium dihydrogen phosphate, magnesium sulfate, ferrous sulfate, manganous sulphate, calcium carbonate, etc. can preferably be used. Trace amounts of various substances like biotin and thiamine also can be added to the medium whenever the strains used in the invention required the above.

Culturing preferably is carried out in aerobic conditions created by stirring or shaking. For example, culturing of the cells on a laboratory scale may be carried out aerobically in 250 ml Erlenmeyer flasks under submerged condition in a rotary shaker with appropriate agitation. Those skilled in the art will be capable of scaling the process to produce commercial quantities of arginine. The temperature for the incubation can be within 20° C. to 50° C., more preferably from 25° C. to 40° C., even more preferably from 27° C. to 36° C., and most preferably from 30° C. to 32° C. It is preferred that the pH of the fermentation, is within the range of from 4 to 9, preferably from 5 to 8, more preferably from 5.5 to 7.5, even more preferably from 6 to 7, and most preferably the pH is maintained near neutrality. Low level (1-5 Units) supplementation of beta lactam antibiotic like penicillin also is preferred to enhance the amino acid efflux. Usually, fermentation lasts for a period of from 12 hours to 2 weeks, preferably from 1 day to 10 days, and most preferably from 2-6 days to accumulate sufficient amounts of arginine depending on the culture condition and initial sugar level.

After fermentation, the arginine present in the fermentation liquor can be separated, for example, by removing microbial cells and any other precipitates by conventional methods such as an ion exchange resin treatment, or precipitation. Qualitative determination of arginine accumulated in the culture broth (fermentation liquor) may be accomplished by TLC and quantification by HPLC after dansyl chloride derivatization. The partial purification and recovery of arginine can be standardized with strongly acidic cation exchange resin such as Amberlite.

Persons having ordinary skill in the art will appreciate that the processes described herein may also produce additional amino acids, such as, for example, Glutamic acid, and other baste L-amino acids or acidic L-amino acids such as Lysine.

Having generally described this invention, a further understanding can be obtained by reference to certain specific examples which are provided herein for purposes of illustration.

Specific Embodiments of the Invention

EXAMPLE 1

An 18 hour inoculum of *Corynebacterium glutamicum* ATCC 831 was inoculated in a fermentation medium with a composition containing Jack fruit seed powder hydrolysate equivalent to 6% dextrose, 0.05% $K_2HOP_4$, 0.05% $KH_2PO_4$, 3% $(NH_4)_2SO_4$, 0.025% $MgSO_4.7H_2O$, 0.001% $FeSO_4.7H_2O$, 0.001% $MnSO_4.4H_2O$, 0.5% Nz-amine, 50 µg/l Biotin, 2 mg/l Thiamine, 500 µl Corn steep liquor and 2% $CaCO_3$. The pH was maintained at neutral. Incubation was carried out for a total of 120 hours at 32° C. with shaking resulting in a final arginine accumulation of 2.27 mg/ml. The amount of arginine produced throughout the 120 hour period was determined at intervals of 24, 48, 72, 96, and 120 hours. The results are shown in Table 3 below:

TABLE 3

Arginine Production by *C. glutomicum* ATCC 21831 in Jack fruit seed hydrolysate

| | Time (hours) | | | | |
|---|---|---|---|---|---|
| | 24 | 48 | 72 | 96 | 120 |
| Arginine Concentration (mg/ml) | 1.05 | 2.05 | 2.10 | 2.15 | 2.27 |

EXAMPLE 2

An L-Arginine producing mutant strain of *Corynebacterium glutamicum* (ATCC 21831) was cultured in a medium composed of 0.5% dextrose, 0.5% sodium chloride, 0.5% yeast extract, 0.5% peptone, 0.2% casein enzyme hydrolysate with shaking for 18 hours to obtain the seed culture for fermentation. The fermentation medium (25 ml) was dispensed in a 250 ml Erlenmeyer flask, inoculated with 5% of the seed culture and incubated at 32° C. in a rotary shaker. The fermentation medium was composed of Cassava bagasse hydrolysate equivalent to 8% dextrose, 0.05% $K_2HOP_4$, 0.05% $KH_2PO_4$, 3% $(NH_4)_2SO_4$, 0.025% $MgSO_4.7H_2O$, 0.001% $FeSO_4.7H_2O$, 0.001% $MnSO_4.4H_2O$, 0.5% Nz-amine, 50 µg/l Biotin, 2 mg/l Thiamine, 500 µl Corn steep liquor, 2% $CaCO_3$. The pH was adjusted to neutral. During the course of incubation a lactam antibiotic was supplemented in the fermentation medium. After 48 hours of incubation, the amount of L-Arginine was accumulated in the fermentation liquor was 1.63 mg/ml, which represented the maximum concentration of L-arginine. The amount of arginine produced throughout the 120 hour period was determined at intervals of 24, 48, 72, 96, and 120 hours. The results are shown in Table 4 below:

TABLE 4

Arginine Production by *C. glutomicum* ATCC 21831 in Cassava bagasse hydrolysate

| | Time (hours) | | | | |
|---|---|---|---|---|---|
| | 24 | 48 | 72 | 96 | 120 |
| Arginine Concentration (mg/ml) | 0.87 | 1.63 | 1.10 | 1.10 | 1.41 |

EXAMPLE 3

For production of L-Arginine by submerged fermentation using a mutant strain of *Corynebacterium glutamicum*, specifically *Corynebacterium glutamicum* ATCC 21493, inoculum was prepared by shaking at 30° C. for 18 hours in a medium composed of 0.5% dextrose, 0.5% sodium chloride, 0.5% yeast extract, 0.5% peptone, 0.2% casein enzyme hydrolysate 0.5% of the inoculum so obtained is transferred to 25 ml batches of the fermentation medium. The above said fermentation medium is an aqueous natural medium composed of Jack fruit seed powder hydrolysate equivalent to 6% dextrose, 0.05% $K_2HOP_4$, 0.05% $KH_2PO_4$, 3% $(NH_4)_2SO_4$, 0.025% $MgSO_4.7H_2O$, 0.001% $FeSO_4.7H_2O$, 0.001% $MnSO_4.4H_2O$, 0.5% Nz-amine, 50 µg/l Biotin, 2 mg/l Thiamine, 500 µl Corn steep liquor and 2% $CaCO_3$.

Fermentation was carried out at 32° C. for 96 hours. A lactam antibiotic was supplemented at the initial stages of incubation. After incubation for 96 hours, a maximum of 1.93 mg/ml of L-arginine was accumulated in the fermentation liquor. The amount of arginine produced throughout the 120 hour period was determined at intervals of 24, 48, 72, 96, and 120 hours. The results are shown in Table 5 below:

TABLE 5

Arginine Production by *C. glutomicum* ATCC 21493 in Jack fruit seed hydrolysate

| | Time (hours) | | | | |
|---|---|---|---|---|---|
| | 24 | 48 | 72 | 96 | 120 |
| Arginine Concentration (mg/ml) | 0.15 | 0.65 | 1.49 | 1.93 | 1.72 |

EXAMPLE 4

Table 6 below shows a comparison of the maximum production of L-Arginine produced by fermentation with *C. glutamicum* ATCC 21831 in different production media under the defined conditions mentioned for the strain, and as described above in Examples 1 and 2. The inventors surprisingly discovered that production of arginine was higher in hydrolysate based medium, in comparison to normal medium where pure dextrose is used as carbon source.

TABLE 6

Production of L-Arginine by by *C. glutomicum* ATCC 21831 in different media

| Media | Normal (pure dextrose) | Cassava bagasse hydrolysate | Jack fruit seed hydrolysate |
|---|---|---|---|
| Arginine Concentration (mg/ml) | 0.45 | 1.63 | 2.27 |

The embodiments described herein provide unique advantages for the production of arginine, as well as an unexpectedly superior yield of arginine from cheap agro-wastes, when compared to the yield from a pure carbon source such as dextrose. On advantage is the use, or recycling of agro residual wastes like cassava bagasse or jack fruit seeds, which otherwise would have remained unutilized and/or discarded. Another advantage is the use of an alternative method to reduce the use of expensive refined sugars like dextrose for fermentation purpose. Yet another advantage is the relatively higher production of arginine in the hydrolysate-based medium, when compared to the more expensive dextrose medium.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

We claim:

1. A method of making arginine by fermentation of agro-wastes wherein said agro-waste is Cassava bagasse, Jack fruit powder, and a mixture thereof, comprising:
    Subjecting the agro-waste to fermentation in the presence of at least one of *Corynebacterium glutamicum* ATCC 21831 or *Corynebacterium glutamicum* ATCC 21493, to produce a fermented liquor,
    wherein the agro-waste is a source of carbon produced by hydrolyzing Cassava bagasse, Jack fruit powder, and a mixture thereof with a starch saccharifying enzyme.

2. The method as claimed in claim 1, wherein the fermentation is aerobic fermentation.

3. The method as claimed in claim 1, wherein the fermentation is conducted at a temperature within the range of from 20° C. to 50° C.

4. The method as claimed in claim 3 wherein the temperature is from 30° C. to 32° C.

5. The method as claimed in claim 1, wherein the fermentation is conducted at a pH within the range of 5 to 8.

6. The method as claimed in claim 5, wherein the pH from 6 to 7.

7. The method as claimed in claim 1, wherein the fermentation is conducted for a period of time of from 12 hours to 2 weeks.

8. The method as claimed in claim 7, wherein the period of time is from 2 days to 6 days.

9. The method as claimed in claim 1, further comprising adding a lactam antibiotic during fermentation.

10. A method of making L-arginine from starch-containing agro-waste materials selected from cassava bagasse, jack fruit seed powder, and mixtures thereof, comprising:
    enzymatically hydrolyzing the agro-waste materials to convert the waste to reducing sugars;
    fermenting the reducing sugars in the presence of at least one of *Corynebacterium glutamicum* ATCC 21831 or *Corynebacterium glutamicum* ATCC 21493 to produce a fermented liquor containing arginine; and
    recovering the arginine from the fermented liquor.

11. The method as claimed in claim 10, wherein enzymatically hydrolyzing the agro-wastes converts from 55 to 85% of the agro-waste to reducing sugars.

12. The method as claimed in claim 10, wherein the fermentation is conducted at a temperature within the range of from 20° C. to 50° C.

13. The method as claimed in claim 12, wherein the temperature is from 30°C. to 32° C.

14. The method as claimed in claim 10, wherein the fermentation is conducted at a pH within the range of 5 to 8.

15. The Method as claimed in claim 14, wherein the pH is from 6 to 7.

16. The method as claimed in claim 10, wherein the fermentation is conducted or a period of time of from 12 hours to 2 weeks.

17. The method as claimed in claim 10, further comprising adding a lactam antibiotic during the fermenting process.

* * * * *